United States Patent [19]

Karrer

[11] 4,276,401

[45] Jun. 30, 1981

[54] N-HETEROCYCLIC SUBSTITUTED ACRYLOYL POLYMERIC COMPOUNDS

[75] Inventor: Friedrich Karrer, Zofingen, Switzerland

[73] Assignee: Ciba-Geigy Corporation, Ardsley, N.Y.

[21] Appl. No.: 82,392

[22] Filed: Oct. 5, 1979

[30] Foreign Application Priority Data

Oct. 13, 1978 [CH] Switzerland .................. 10647/78

[51] Int. Cl.$^3$ ............... C08F 220/34; C08F 220/54; C08F 220/60
[52] U.S. Cl. ......................... 526/263; 204/159.22; 526/259; 526/265
[58] Field of Search .................. 526/259, 263, 265; 204/159.22

[56] References Cited

U.S. PATENT DOCUMENTS 2,727,021  12/1955  Price ................................. 526/263
3,705,166  12/1972  Murayama et al. .
3,901,849   8/1975  Dodson et al. ............ 260/45.8 NW

FOREIGN PATENT DOCUMENTS 1112439  5/1968  United Kingdom .

OTHER PUBLICATIONS

European Search Report 496.
European Search Report 1803.

Primary Examiner—Harry Wong, Jr.
Attorney, Agent, or Firm—Harry Falber

[57] ABSTRACT

Copolymeric compounds which carry side N-heterocyclic rings and contain the recurring structural unit of the formula (I)

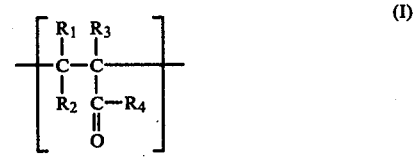

in which $R_1$ and $R_2$ are hydrogen and $R_3$ is hydrogen or $C_1$–$C_4$ alkyl and $R_4$ is a N-heterocyclic substituent, their preparation and their use as light stabilizers and UV absorbers in organic material and also the organic material stabilized with the aid of these compounds.

11 Claims, No Drawings

N-HETEROCYCLIC SUBSTITUTED ACRYLOYL POLYMERIC COMPOUNDS

The present invention relates to novel polymeric compounds, their preparation and their use as light stabilisers and UV absorbers in organic material and to the organic material stabilised with the aid of these compounds.

It is known from U.S. Pat. No. 3,705,166 to use monomeric acrylic acid derivatives which contain at least one piperidinyl group with a sterically hindered nitrogen atom as light stabilisers in organic polymers. These acrylic acid derivatives are, however, too readily volatile. Furthermore, the possibility of incorporating the monomeric additive in certain substrates is also mentioned. This, however, has the disadvantage that the polymer structure is disturbed by the additive incorporated and this can result in the characteristics of the substrate to be protected being changed in a manner difficult to control. Water-soluble polymeric acrylic and methacrylic acid derivatives have been proposed as flocculating agents in Japanese Published Specification No. 49-75,469.

Further compounds which have been described as UV absorbers are homopolymeric 2-hydroxy-4-acryloylethoxybenzophenones in U.S. Pat. No. 3,365,421, homopolymeric 2-(2′-hydroxyphenyl)-benztriazoles in U.S. Pat. No. 3,399,173 and polymeric alkenoyloxybenzylidene-malonic acid esters in U.S. Pat. No. 3,943,094.

Copolymeric additives have now been found which, in addition to excellent light-stabilising properties, good solubility or compatibility in the polymer to be protected and high stability to extraction and migration, at the same time have a powerful UV-absorber action.

The present invention relates to copolymeric compounds which carry side N-heterocyclic rings and contain the recurring structural unit of the formula (I)

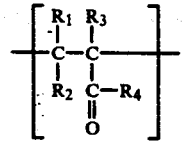

in which $R_1$ and $R_2$ are hydrogen and $R_3$ is hydrogen or $C_1$–$C_4$ alkyl and $R_4$ is a N-heterocyclic substituent of the formulae (II), (III), (IV) or (V)

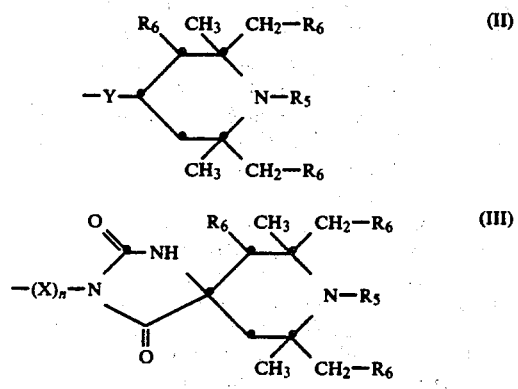

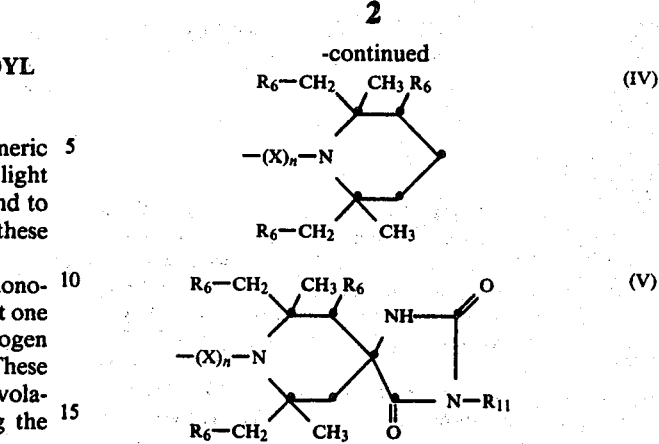

in which $R_5$ is hydrogen, oxyl, $C_1$–$C_{18}$ alkyl, $C_3$–$C_8$ alkenyl, $C_3$–$C_6$ alkynyl, $C_7$–$C_{12}$ aralkyl, $C_2$–$C_{21}$ alkoxyalkyl, cyanomethyl, an aliphatic acyl group having 1 to 4 carbon atoms or a group —$CH_2COOR_7$, in which $R_7$ is $C_1$–$C_{12}$ alkyl, $C_3$–$C_8$ alkenyl, phenyl, $C_7$–$C_8$ aralkyl or cyclohexyl, and $R_6$ is hydrogen or methyl and Y is —O— or

in which $R_9$ is hydrogen, $C_1$–$C_{12}$ alkyl, $C_5$–$C_8$ cycloalkyl or $C_7$–$C_{12}$ aralkyl, and X is a group of the formula —O—CH($R_{10}$)—$CH_2$— (VI), in which $R_{10}$ is hydrogen, methyl, ethyl, phenoxymethyl or phenyl, and n is 0 or 1, and $R_{11}$ is $C_1$–$C_{18}$ alkyl allyl, cyclohexyl, phenyl, benzyl or a group of the formula —$CH_2$—$COOR_{12}$ (VII), in which $R_{12}$ is $C_1$–$C_8$ alkyl, and, furthermore, $R_4$ is one of the groups of the formulae (VIII), (IX), (X) or (XI)

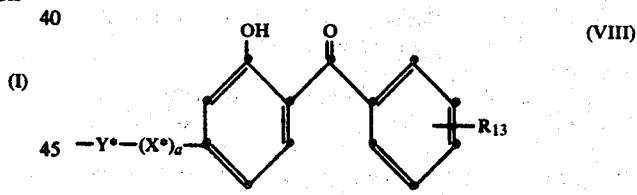

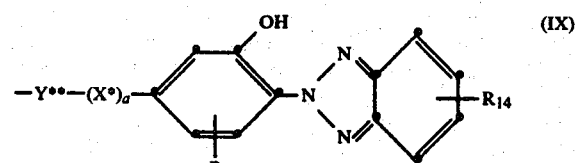

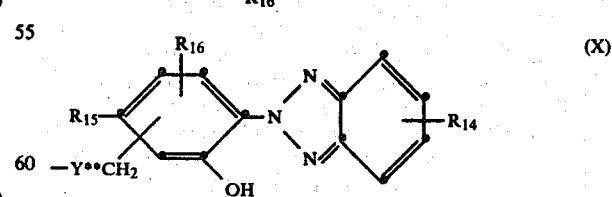

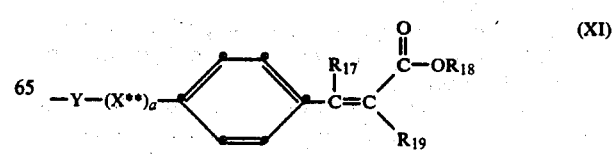

in which Y and Y☆☆ have the meaning defined above for Y, and Y. is —O— or

in which $R_9$ ☆ is hydrogen or $C_1$–$C_8$ alkyl, and X ☆ is a group of the formula —CH($R_{10}$)—($CH_2$)$_b$—O— (XII), in which b is 1 or 2 and $R_{10}$ is as defined above, and a is 0 or 1, and $R_{13}$ is hydrogen, methyl or chlorine and $R_{14}$ is hydrogen, methyl, methoxy or chlorine and $R_{15}$ is hydrogen or hydroxyl and $R_{16}$ is hydrogen, $C_1$–$C_{12}$ alkyl, $C_5$–$C_8$ cycloalkyl, phenyl, $C_7$–$C_{12}$ aralkyl or chlorine and X ☆☆ is a group of the formula (XII), in which $R_{10}$ is as defined above and b is 1, and $R_{17}$ is hydrogen or $C_1$–$C_4$ alkyl and $R_{18}$ is $C_1$–$C_{12}$ alkyl, $C_5$–$C_8$ cycloalkyl or a group of the formula (XIII)

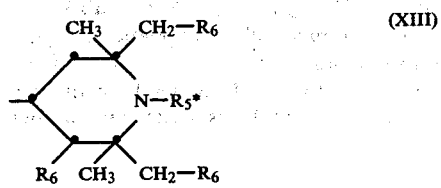

in which $R_5$ ☆ is hydrogen, $C_1$–$C_8$ alkyl, $C_3$–$C_8$ alkenyl, $C_7$–$C_{12}$ aralkyl or an aliphatic acyl group having 1 to 4 carbon atoms and $R_6$ is as defined above, and $R_{19}$ is —CN or a group of the formula —COO$R_{18}$ (XIV), in which $R_{18}$ is as defined above, with the proviso that, in the copolymeric molecule containing the recurring structural unit I, at least one (A) of the substituents $R_4$ is one of the groups of the formula (II), (III), (IV) or (V) and at least one (B) of the substituents $R_4$ is one of the groups of the formulae (VIII), (IX), (X) or (XI), (A):(B) being in a ratio of 50:1 to 1:50. $C_1$–$C_4$ alkyl $R_3$ can be, for example, methyl, ethyl, n-propyl or n-butyl; preferably, $R_3$ is hydrogen or methyl. $R_4$ can be one of the groups of the formulae (II), (III), (IV), (V), (VIII), (IX), (X) or (XI). Groups of the formulae (II), (IV), (VIII), (IX) and (X) are preferred.

$C_1$–$C_{18}$ alkyl $R_5$ is, for example, methyl, ethyl, n-propyl, n-butyl, n-pentyl, n-octyl, n-decyl, n-dodecyl or octadecyl. Preferred alkyl groups are those having 1 to 12 carbon atoms, also those having 1 to 8 carbon atoms and especially those having 1 to 4 carbon atoms and in particular methyl.

$C_3$–$C_8$ alkenyl $R_5$ is, for example, allyl, 3-methyl-2-butenyl, 2-butenyl, 2-hexenyl or 2-octenyl, especially allyl.

$C_3$–$C_6$ alkynyl $R_5$ is, for example, propargyl.

$C_7$–$C_{12}$ aralkyl $R_5$ is, for example, benzyl, β-phenylethyl or 4-tert.-butyl-benzyl, preferably benzyl.

In $C_2$–$C_{21}$ alkoxyalkyl $R_5$, the alkyl part can contain 1 to 3 carbon atoms and the alkoxy part can consist of 1 to 18 carbon atoms, as, for example, in methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl; particularly preferred compounds are those in which $R_5$ is an alkoxyalkyl group having 2 to 6 carbon atoms.

As an aliphatic acyl group having 1 to 4 carbon atoms, $R_5$ is, for example, formyl, acetyl, acryloyl or crotonoyl, especially acetyl.

In a —$CH_2COOR_7$ group $R_5$, $C_1$–$C_{12}$ alkyl $R_7$ is, for example, methyl, ethyl, isopropyl, n-butyl, isobutyl, t-butyl, isopentyl, n-octyl or n-dodecyl. Preferably, $R_7$ is $C_1$–$C_4$ alkyl. $C_3$–$C_8$ alkenyl $R_7$ is, for example, allyl, 2-butenyl or 2-hexenyl. $C_7$–$C_8$ aralkyl $R_7$ is, for example, benzyl or α-phenylethyl. $R_6$ can be methyl and preferably hydrogen and Y is

and preferably —O—.

$C_1$–$C_{12}$ alkyl $R_9$ and $R_{18}$ are, for example, methyl, ethyl, n-propyl, n-butyl, n-pentyl, n-octyl, n-decyl or n-dodecyl, but preferably $C_1$–$C_4$ alkyl.

$C_7$–$C_{12}$ aralkyl $R_9$ and $R_{16}$ are especially α,α-dimethyl-benzyl, benzyl or, in particular, α-methylbenzyl. $C_5$–$C_8$ cycloalkyl $R_9$, $R_{16}$ and $R_{18}$ are, for example, cyclopentyl, cycloheptyl, cyclooctyl and preferably cyclohexyl. $R_{10}$ is phenyl or phenoxymethyl, preferably methyl or ethyl and in particular hydrogen. $C_1$–$C_{18}$ alkyl $R_{11}$ is, for example, methyl, ethyl, propyl, butyl, hexyl, octyl, dodecyl or octadecyl. Preferred alkyl groups are those having 1 to 12 carbon atoms. $R_{11}$ can also be benzyl, cyclohexyl or phenyl.

$C_1$–$C_8$ alkyl $R_9$ ☆ and $R_{12}$ are, for example, methyl, ethyl, n-propyl, n-butyl, n-hexyl or n-octyl and $R_9$☆ preferably has 1 to 4 carbon atoms. Y ☆ is preferably —O—.

In preferred compounds, $R_{13}$, $R_{14}$ and $R_{15}$ are hydrogen. In preferred compounds, $R_{13}$ is in the 4'-position, whilst $R_{14}$ is preferably in the 5-position. $R_{16}$ can be alkyl having 1 to 12 carbon atoms and preferably having 1 to 8 carbon atoms, such as methyl, ethyl, iso-propyl, iso-butyl, t.-butyl, iso-pentyl, t.-amyl, hexyl, 1,1,3,3-tetramethylbutyl or 1,1,3,3,5,5-hexamethylhexyl. In preferred compounds, $R_{16}$ is bonded in the 5'-position, whilst the group —$CH_2$—Y ☆☆ is preferably in the 3'-position on the 2-(2'-hydroxyphenyl)-benztriazole system or also in the 5'-position if this is not occupied by substituent $R_{16}$.

$C_1$–$C_4$ alkyl $R_{17}$ can be ethyl, n-propyl or n-butyl; preferably, however, it is methyl.

$R_{17}$ is preferably alkyl if $R_{19}$ is —CN and is preferably hydrogen if $R_{19}$ is a group of the formula (XIV).

If $R_{18}$ is a group of the formula (XIII), $R_5$ ☆ can, within the given limits, assume the meanings defined above for $R_5$.

The compounds containing the recurring structural unit of the formula (I) are copolymers which are obtained by copolymerisation of at least two monomeric components, specifically in such a way that, in the macromolecular molecule, at least one (A) $R_4$ is one of the groups of the formula (II), (III), (IV) or (V) and at least one (B) $R_4$ is one of the groups of the formulae (VIII), (IX), (X) or (XI), (A):(B) being in a molecular ratio of 50:1 to 1:50. The ratio of the structural units (A) in which $R_4$ is a group of the formula (II), (III), (IV) or (V) to the structural units (B) in which $R_4$ is a group of the formula (VIII), (IX), (X) or (XI) is preferably 10:1 to 1:10 and especially 5:1 to 1:5 and particularly preferentially 3:1 to 1:3.

Of course, copolymers of more than two monomeric components, for example terpolymers, can also be used.

The third component present in the terpolymers can satisfy the above condition (A) or (B) or can comprise other polymerisable monomers. By this means it is possible, in a simple manner, to exert an influence on the characteristics, such as the solubility or the softening point of the additive. Suitable copolymerisable ter-components are, therefore, for example styrene, divinylbenzene, 2- or 4-vinylpyridine and compounds of the acrylic acid series, such as esters or amides which are derived from acrylic acid or methacrylic acid, for example methyl acrylate, butyl acrylate, methyl methacrylate, acrylonitrile, methacrylonitrile, acrylic acid glycidyl ester, methtylenebisacrylamide or ethtylene glycol dimethacrylate; alternatively these components can be 1-alkenes having 2–10 C atoms, for example ethylene, propylene, 1-butene, 1-pentene, 1-hexene, 1-octene or 1-decene; furthermore, the components can be isoprene, butadiene, vinyl esters, such as vinyl acetate, vinyl ethers, N-vinyl-2-pyrrolidone, N-vinylcarbazole, maleimides or unsaturated phosphonates. Preferred copolymerisable components are styrene, acrylonitrile, acrylates or methacrylates, vinyl esters, vinyl ethers or acrylamides or methacrylamides.

The molecular weight of the copolymers according to the invention is preferably above 500; however, it can by all means be up to 150,000. Preferred compounds have a molecular weight of 500 to 60,000 and in particular of 1,000 to 20,000.

Preferred copolymeric compounds containing the recurring structural unit of the formula (I) are those in which $R_1$ and $R_2$ are hydrogen and $R_3$ is hydrogen or methyl and $R_4$ is a group of the formulae (II), (III), (IV) or (V), in which $R_5$ is hydrogen, $C_1$–$C_{12}$ alkyl, allyl, propargyl, benzyl, acetyl or $C_2$–$C_6$ alkoxyalkyl and $R_6$ is hydrogen or methyl and y is —O— or $$-\overset{|}{N}-R_9,$$

in which $R_9$ is hydrogen, $C_1$–$C_{12}$ alkyl, cyclohexyl or benzyl, and ☆ is a group of the formula (VI), in which $R_{10}$ is hydrogen, methyl or ethyl, and n is 0 or 1, and $R_{11}$ is $C_1$–$C_{12}$ alkyl, allyl or benzyl, and, furthermore, $R_4$ is a group of the formulae (VIII), (IX), (X) or (XI), in which Y and Y☆☆ have the meaning defined above for Y, and Y☆ is —O— or $$-\overset{|}{N}-R_9\text{☆},$$

in which $R_9$ ☆ is hydrogen or $C_1$–$C_4$ alkyl, and X ☆ is a group of the formula (XII), in which $R_{10}$ is as defined above, and b is 1 or 2, and a is 0 or 1, $R_{13}$ is hydrogen, methyl or chlorine and $R_{14}$ and $R_{15}$ are hydrogen and $R_{16}$ is hydrogen, $C_1$–$C_8$ alkyl, cyclohexyl, phenyl, $C_7$–$C_9$ aralkyl or chlorine, and X ☆☆ and $R_{17}$ are as defined above and $R_{18}$ is $C_1$–$C_8$ alkyl, cyclohexyl or a group of the formula (XIII), in which $R_5$ ☆ is hydrogen, $C_1$–$C_8$ alkyl, allyl, benzyl or acetyl and $R_6$ is as defined and $R_{19}$ is —CN or a group of the formula (XIV), in which $R_{18}$ is as defined above, with the proviso that, in the copolymeric molecule containing the recurring structural unit I, at least one (A) $R_4$ is one of the groups (II), (III), (IV) or (V) and at least one (B) $R_4$ is one of the groups of the formulae (VIII), (IX), (X) or (XI), (A):(B) being in a ratio of 50:1 to 1:50.

Preferred copolymeric compounds containing the recurring structural unit of the formula (I) are those in which $R_1$ and $R_2$ are hydrogen and $R_3$ is hydrogen or methyl and $R_4$ is a group of the formulae (II) or (IV), in which $R_5$ is hydrogen, $C_1$–$C_8$ alkyl, allyl, benzyl or acetyl and $R_6$ is hydrogen and Y is —O— or $$-\overset{|}{N}-R_9,$$

in which $R_9$ is hydrogen or $C_1$–$C_4$ alkyl, and X is a group of the formula (VI), in which $R_{10}$ is hydrogen or methyl, and n is 0 or 1, and, furthermore, $R_4$ is a group of the formulae (VIII), (IX), (X) or (XI), in which Y is as defined above and Y ☆ is $$-\overset{|}{N}-R_9,$$

in which $R_9$ is as defined above, and Y ☆ is —O— and X ☆ and X ☆☆ are a group of the formula (XII), in which $R_{10}$ is as defined above and b is 1, and a is 0 or 1, and $R_{13}$, $R_{14}$ and $R_{15}$ are hydrogen and $R_{16}$ is H, $C_1$–$C_8$ alkyl or $C_7$–$C_9$ aralkyl and $R_{17}$ is $C_1$–$C_4$ alkyl if $R_{19}$ is —CN or is hydrogen if $R_{19}$ is a group of the formula (☆ IV), and $R_{18}$ is $C_1$–$C_8$ alkyl or a group of the formula (☆ III), in which $R_5$ ☆ is hydrogen, $C_1$–$C_4$ alkyl, benzyl or acetyl, and $R_4$ is as defined above, and $R_{19}$ is —CN or a group of the formula (☆ IV), in which $R_{18}$ is as defined above, with the proviso indicated above for $R_4$.

Further preferred copolymeric compounds containing the recurring structural unit of the formula (I) are those in which $R_1$ and $R_2$ are hydrogen and $R_3$ is hydrogen or methyl and $R_4$ is a group of the formulae (II) or (IV), in which $R_5$ is hydrogen, $C_1$–$C_4$ alkyl, benzyl or acetyl and $R_6$ is hydrogen and Y is —O— or $$-\overset{|}{N}-R_9,$$

in which $R_9$ is hydrogen or $C_1$–$C_4$ alkyl, and ☆ is a group of the formula (VI), in which $R_{10}$ is hydrogen or methyl, and n is 0 or 1, and, furthermore, $R_4$ is a group of the formulae (VIII), (☆ ) or (☆ I), in which Y and Y ☆ are —O— and Y is $$-\overset{|}{N}-R_9,$$

in which $R_9$ is as defined above, and X ☆ and X ☆☆ are a group of the formula (☆ II), in which $R_{10}$ is as defined above and b is 1, and a is 0 or 1, and $R_{13}$, $R_{14}$ and $R_{15}$ are hydrogen and $R_{16}$ is H, $C_1$–$C_8$ alkyl or $C_7$–$C_9$ aralkyl and $R_{17}$ is methyl if $R_{19}$ ☆ is —CN or is hydrogen if $R_{19}$ is a group of the formula (☆ IV), and $R_{18}$ is $C_1$–$C_8$ alkyl or a group of the formula (☆ III), in which $R_5$ ☆ is hydrogen or methyl and $R_6$ ☆ is hydrogen, and $R_{19}$ is —CN or a group of the formula (☆ IV), in which $R_{18}$ is as defined above, with the proviso indicated above for $R_4$.

Particularly preferred copolymeric compounds containing the recurring structural unit of the formula (I) are those in which $R_1$ and $R_2$ are hydrogen and $R_3$ is hydrogen or methyl and $R_4$ is a group of the formulae (II) or (IV), in which $R_5$ is hydrogen, methyl or acetyl and $R_6$ is hydrogen and Y is —O— or

in which $R_9$ is hydrogen or $C_1$-$C_4$ alkyl, and ☆ is a group of the formula (VI), in which $R_{10}$ is hydrogen, and n is 0 or 1, and, furthermore, $R_4$ is a group of the formulae (VIII) or (☆), in which Y☆ is —O— and Y☆☆ is

in which $R_9$ is as defined above, and ☆ and X ☆☆ are a group of the formula (☆II), in which $R_{10}$ is as defined above and b is 1, and $R_{13}$, $R_{14}$ and $R_{15}$ are hydrogen and $R_{16}$ is H, $C_1$-$C_8$ alkyl or $C_7$-$C_9$ aralkyl, with the proviso indicated above for $R_9$.

The copolymers containing the recurring structural unit of the formula (I) are prepared by known polymerisation reactions, which are described, for example, in Houben-Weyl, 14 (1) 1,010–1,078 (1962). For example, a monomer of the formula (☆Va)

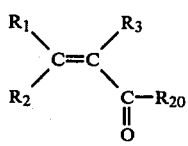 (☆Va)

is copolymerised with a monomer of the formula (☆Vb)

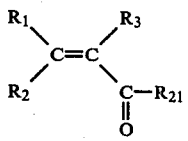 (☆Vb)

in which formulae $R_{20}$ is a group of the formulae (II), (III), (IV) or (V) defined above and $R_{21}$ is a group of the formulae (VIII), (I ☆ ), (☆ ) or (☆ I) defined above, and the ratio of monomer (☆ Va) to monomer (☆ Vb) should be 50:1 to 1:50. In the formulae (☆ Va) and (☆ Vb), the substituents $R_1$, $R_2$ and $R_3$ are as defined above.

The monomers of the formula (☆ Va), which are used in the polymerisation, are prepared in a manner known per se, for example analogously to the methods described in U.S. Pat. No. 3,705,166. For example, a reactive derivative of an unsaturated carboxylic acid of the formula (☆ VI)

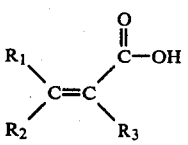 (☆VI)

is reacted with one of the compounds of the formulae (II ☆ ), (III ☆ ), (IV ☆ ) or (V ☆ )

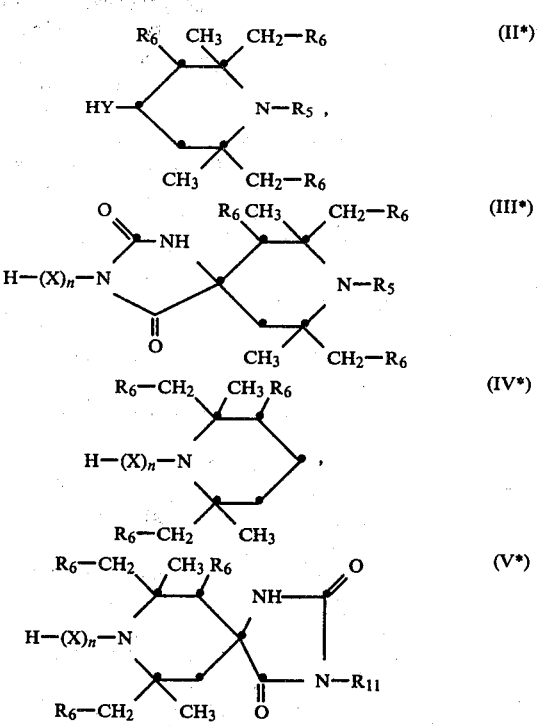

in which all the substituents are as defined above, preferably in an inert organic solvent.

Reactive derivatives of an unsaturated carboxylic acid are, for example, an acid halide of the formula (☆ VIa)

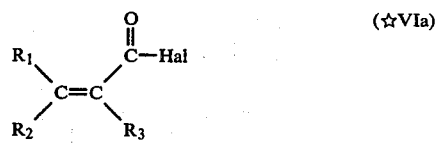 (☆VIa)

in which Hal is bromine or in particular chlorine, or an acid anhydride of the formula ( VIb)

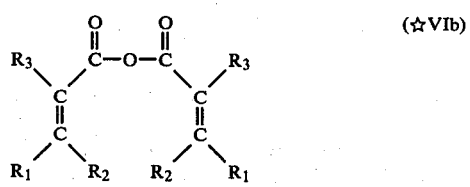 (☆VIb)

Preferably, approximately one mol of a compound of the formula (☆ VIa) or (☆ VIb) is employed per mol of one of the compounds of the formula (II ☆ ), (III ☆ ), (IV ☆ ) or (V ☆ ). In the formulae (☆ VIa) and (☆ VIb), $R_1$, $R_2$ and $R_3$ are as defined above.

When an acid halide of the formula (☆ VIa) is used, the reaction is carried out in the presence of a base, for example in the presence of a tertiary amine, such as triethylamine, di-isopropyl-ethylamine, N,N-diethylaniline or pyridine, or in the presence of an anhydrous alkali metal carbonate or alkaline earth metal carbonate or alkali metal bicarbonate, such as $MgCO_3$, $NaHCO_3$, $Na_2CO_3$ or $K_2CO_3$. If an acid anhydride of the formula (☆ VIb) is used in place of the acid chloride, the base can be dispensed with in some cases.

The organic solvents used in the process variants described above must be inert towards the reactants. Suitable solvents are, for example, aliphatic hydrocarbons, such as hexane or ligroin, aromatic hydrocarbons, such as benzene, toluene or xylene, chlorinated hydrocarbons, such as methylene chloride, chloroform or 1,2-dichloroethane, amides, such as hexamethylenephosphoric acid triamide, or ethers, such as dioxan, 1,2-dimethoxyethane, diethyl ether or tetrahydrofuran.

The temperature for this reaction is preferably −20° to +120° C. but in particular −10° C. to +80° C.

A further process variant comprises using, as the reactive derivative of a carboxylic acid of the formula (☆VI), an ester of the formula (☆VIc)

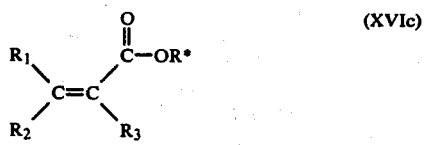

in which $R_1$, $R_2$ and $R_3$ are as defined above and R☆ is $C_1$-$C_4$ alkyl. The reactants of the formulae (II☆), (III☆), (IV☆) or (V☆), in which n is 1 and the other symbols are as defined above, can be reacted in approximately stoichiometric amounts or with an excess of (☆VIc).

This method is a conventional trans-esterification method, the reaction taking place at elevated temperature, with or without a solvent and in the presence of a trans-esterification catalyst, for example an acid or preferably a base such as titanium tetrabutyrate, titanium tetrapropionate, aluminium isopropoxide, lithium amide, lithium hydride or sodium hydride. The temperature is preferably 20° to 170° C. and in particular 50° to 150° C. If the reaction is carried out in a solvent, one of the abovementioned solvents can be used. An ion exchange resin can also be employed as the catalyst. Since the compounds of the formula (☆VIc) are liquid compounds, a solvent can be dispensed with if desired. If necessary, the reactant (☆VIc) must be stabilised with one of the known stabilisers, for example hydroquinone, hydroquinone monomethyl ether, 2,6-di-tert.-butyl-p-cresol, another 2,6-di-tert.-butyl-phenyl derivative or phenothiazine, before the trans-esterification reaction.

The compounds of the formulae (☆VI), (☆VIa), (☆VIb) and (☆VIc) used as starting materials are compounds known to those skilled in the art and, if not available commercially, can be prepared in a simple way.

The piperidinyl derivatives used as reactants are likewise known compounds. The preparation of the compounds of the formula (II☆) has been described, for example in German Offenlegungsschrift No. 2,352,658 (4-hydroxy-piperidines) or in U.S. Pat. No. 3,684,765 (4-aminopiperidines).

The compounds of the formulae (III☆) and (V☆) can be prepared analogously to the methods described in German Offenlegungsschrift No. 2,227,689.

The preparation of compounds of the formula (IV☆) is known, for example from German Offenlegungsschrift No. 2,418,540.

The compounds of the formulae (II☆), (III☆), (IV☆) and (V☆), which have substituents of different types in the 2-position and the 6-position in the piperidyl ring, can be prepared by reacting a ketone of the formula $CH_3$—CO—$CH_2$—$R_6$ with ammonia. The pyrimidine formed is hydrolysed, as described in Helv. Chim. Acta 30, 114 (1947), to an aminoketone of the formula (☆VII).

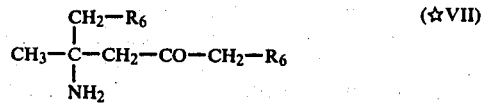

In a second process step, the compounds of the formula (☆VII) are reacted with ammonia and a ketone $CH_3$—CO—$CH_2$—$R_6$, as is described, for example, in Monatsh. Chemie 88, 464 (1957). In the indicated formulae, $R_6$ is as defined above. The compounds of the formulae (II☆) and (III☆) in which $R_5$ is hydrogen can be obtained from the resulting pyrimidine by hydrolysis.

The compounds which carry substituents other than hydrogen in the 1-position and/or 4-position are prepared analogously to the methods described in the literature references quoted above.

The monomers of the formula (☆Vb), which are used for copolymerisation, are also prepared in a known manner.

Thus, for example, the preparation of monomers of the formula (XVb) in which $R_{21}$ is a group of the formula (VIII) is described in U.S. Pat. No. 3,365,421. Usually, these compounds are obtained by esterification of acrylic or methacrylic acid with the corresponding 2-hydroxy-4-(2'-hydroxyethoxy)- or 2,4-dihydroxybenzophenones.

The benztriazole derivatives of the formula (XVb) in which $R_{21}$ is a group of the formula (IX) or (X) are prepared analogously to the methods described in U.S. Pat. No. 3,399,173.

The preparation of the monomers of the formula (XVb) in which $R_{21}$ is a group of the formula (XI) is described in detail in, for example, Org. Reactions, Vol. XV, 332 (1967) or in U.S. Pat. No. 3,943,094.

Monomers of the formula (XVa) which are suitable for the preparation of the copolymeric additives according to the invention are, for example, 1,2,2,6,6-pentamethyl-4-acryloyloxy-piperidine, 1-methacryloyloxyethyl-2,2,6,6-tetramethyl-piperidine, 1-acryloyloxyethyl-2,2,6,6-tetramethyl-piperidine, 1,2,2,6,6-pentamethyl-4-maleimido-piperidine, 1-acetyl-2,2,6,6-tetramethyl-4-maleimido-piperidine, 1-benzyl-2,2,6,6-tetramethyl-4-maleimido-piperidine, 1,3,8-triaza-2,4-dioxo-3-acryloyloxyethyl-7,7,8,9,9-pentamethyl-spiro-[4,5]-decane, 1,3,8-triaza-2,4-dioxo-3-methacryloyl-oxyethyl-7,7,8,9,9-pentamethyl-spiro-[4,5]-decane, 1,3,8-triaza-2,4-dioxo-3-n-dodecyl-7,7,9,9-tetramethyl-8-methacryloyl-oxyethyl-spiro-[4,5]-decane, 1,3,8-triaza-2,4-dioxo-3-methacryloyl-oxyethyl-7,7,9,9-tetramethyl-8-benzyl-spiro[4,5]-decane, 1,3,8-triaza-2,4-dioxo-3-n-butyl-7,7,9,9-tetramethyl-8-acryloyl-oxyethyl-spiro-[4,5]-decane, 1-benzyl-2,2,6,6-tetramethyl-4-(N-n-butyl)-methacrylamido-piperidine, 1,2,2,6,6-pentamethyl-4-(N-benzyl)-acrylamido-piperidine, 1,2,2,6,6-pentamethyl-4-(N-n-propyl)-acrylamido-piperidine, 1,2,2,6,6-pentamethyl-4-(N-n-propyl)-methacrylamidopiperidine, 1-allyl-2,2,6,6-tetramethyl-4-acryloyloxypiperidine, 1-allyl-2,2,6,6-tetramethyl-4-methacryloyloxy-piperidine, 1,2,2,6,6-pentamethyl-4-acrylamidopiperidine, 1-benzyl-2,2,6,6-tetramethyl-4-(N-n-butyl)-acrylamido-piperidine, 1-benzyl-2,2,6,6-tetramethyl-4-acrylamido-piperidine, 1-[3'-acryloyloxy-(2'-hydroxy)-propyl]-2,2,6,6-tetramethyl-piperidine, 2,2,6,6-tetramethyl-4- acryloyloxy-piperidine and 1-benzyl-2,2,6,6-tetramethyl-4-acryloyloxy-piperidine.

Monomers of the formula (XVb) which are suitable for the preparation of the copolymeric additives according to the invention are, for example: 2-hydroxy-4-(2'-acryloyloxyethoxy)-benzophenone, 2-hydroxy-4-(2'-methacryloyloxyethoxy)-benzophenone, 2-hydroxy-4-(2'-acryloyloxy-2'-methylethoxy)-benzophenone, 2-hydroxy-4-(2'-methacryloyloxyethoxy)-4'-methyl-benzophenone, 2-hydroxy-4-(2'-acryloylamido-ethoxy)-benzophenone, 2-hydroxy-4-(methacryloyloxy)-benzophenone, 2-(2'-hydroxy-3'-methacryloylamidomethyl-5'-cyclohexylphenyl)-benztriazole, 2-(2'-hydroxy-3'-acryloylamido-phenyl)-5-chloro-benztriazole, 2-(2'-hydroxy-3'-acryloylamidomethyl-5'-tert.-butylphenyl)-benztriazole, 2-(2'-hydroxy-3'-methacryloylamidomethyl-5'-methyl-phenyl)-benztriazole, 2-(2'-hydroxy-5'-acryloylbenzylamidophenyl)-benztriazole, 2-(2'-hydroxy-4'-[2''-methacryloyloxyethoxy]-phenyl)-benztriazole, 2-(2,4-di-hydroxy-3'-acryloylamidomethyl-phenyl)-benztriazole, diethyl 4-acryloyloxy-benzylidene-malonate, di-n-octyl 4-methacryloyl-ethoxy-benzylidene-malonate, methyl [4-(acryloyloxy-ethoxy)-α-methylbenzylidene]-cyanoacetate, ethyl 2-cyano-3-methyl-3-(4-acryloyloxy-phenyl)-acrylate, diethyl 4-hydroxy-benzylidene malonate and 1,2,2,6,6-pentamethyl-piperidin-4-yl (4-acryloyloxy-benzylidene)-cyanoacetate.

Reactions suitable for the preparation of the copolymeric additives containing the recurring structural unit of the formula (I) are, in particular those known under the names free radical and ionic homo- and co-polymerisation. The polymerisation is controlled in a known manner by initiators and regulators or chain stoppers. By this means it is possible to obtain polymers of the desired molecular weight. The reaction can be carried out in bulk, in solution, in dispersion, in emulsion or in suspension or as a so-called bead polymerisation.

Suitable initiators for free radical homo- and co-polymerisation are, in particular, per compounds, azo compounds and redox systems. Organic or inorganic per compounds commonly used are, inter alia, hydroperoxides, dialkyl peroxides, diacyl peroxides, peresters or peroxodisulphates. Examples of per compounds are hydrogen peroxide, potassium peroxodisulphate, cumene hydroperoxide, di-t.-butyl peroxide, ethyl methyl ketone peroxide, cyclohexanone peroxide, t.-butyl perbenzoate or dibenzoyl peroxide, which is unsubstituted or substituted by chlorine or bromine. Suitable azo compounds are in particular those in which the azo group is bonded on both sides to tertiary carbon atoms which, in addition to alkyl groups, also carry nitrile or ester groups. $\alpha,\alpha'$-Azoisobutyrodinitrile and tert.-butyl perbenzoate are important representatives of this category of initiators. If the poly reaction is initiated by means of a redox system, suitable oxidising agents are organic or inorganic per compounds and suitable reducing agents are either metal ions of low valency or metal-free compounds which can be oxidised easily. Examples of oxidising agents are hydrogen peroxide, peroxydisulphates or diacyl peroxides. Suitable reducing agents are $Ag^+$, $Fe^{2+}$, $Ti^{3+}$, bisulphite, sulphite, thiosulphate, mercaptans, sulphines, amines, endiols (sugars), benzoin/$Fe^{2+}$ or bisulphite/$Fe^{2+}$. Whilst in the case of the per compounds and the azo compounds the nature of the initiator influences only the polymerisation rate, the average degree of polymerisation, the nature of the end groups or the number of branches, but not the polymerisability, not every redox system is suitable for every unsaturated compound.

The molecular weight of the polymer is most simply controlled by means of suitable regulators. Examples are mercaptans, such as n-butyl-mercaptan or dodecyl-mercaptan, and other organic sulphur compounds, such as diisopropylxanthic disulphide, and also aliphatic aldehydes and acetals or allyl compounds, such as allyl alcohol. The reaction temperatures are known to those skilled in the art and for free radical polymerisation, which is preferably used, are 40° C. to 160° C. and preferably 60° C. to 130° C., depending on the nature of the components used.

If the polymerisation is carried out as an ionic reaction, it can be cationic polymerisation, but preferably anionic polymerisation.

Suitable initiators are metal-organic compounds, such as diethyl-zinc or diisobutyl-zinc, naphthalene-sodium, n-amyl-sodium, cyclopentadienyl-sodium, n-butyllithium or triethyl-aluminium. Bases, such as alkali metal hydroxides, alkali metal alcoholates and alkali metal amides, also act as initiators. Instead of the regulators which are employed in the case of free radical polymerisation, substances which react with the growing end of the chain are employed in the case of ionic polymerisation; these substances include, for example, water, alchols, acid and amines. The temperature for this reaction variant is from $-100°$ C. to $+200°$ C. and preferably $-20°$ C. to $+150°$ C. and the temperature for the particular type of polymer desired is known to those skilled in the art.

It is furthermore also possible to use heat, light or other energy-rich radiation as initiators for the polymerisation. In this case, the reaction proceeds by the free radical mechanism. In the case of photo-initiated polymerisation, suitable catalysts are, for example, benzoin ethers, benzil ketals, ω-dialkoxyacetophenone derivatives or aromatic ketone/amine combinations.

Depending on the copolymerisation parameters chosen, statistical copolymers or block copolymers are obtained in this way.

Whilst the copolymerisation of two monomers, and the effects associated therewith, have been investigated particularly well, it is also useful in certain cases to employ polymers of three or more polymerisable compounds.

The compounds containing the recurring structural unit of the formula (I) can be used, according to the present invention, as stabilisers for plastics in order to prevent these being damaged by the action of oxygen, heat and light. Examples of such plastics are the polymers listed on pages 12 to 14 of German Offenelegungsschrift No. 2,456,864.

The stabilisation of polyolefins, styrene polymers, polyamides and polyurethanes is of particular importance and the compounds of the formula (I) are outstandingly suitable for this. Examples of such polymers are high density and low density polyethylene, polypropylene, ethylene/propylene copolymers, polyvinyl chloride, polystyrene, styrene/butadiene/acrylonitrile tercopolymers, mixtures of polyolefins or of styrene polymers, and polyurethanes based on polyethers or polyesters, in the form of lacquers, filaments, sheets, panels, films, elastomers or foams, lacquers based on thermoplastic acrylic resins, crosslinkable acrylic, poly-ester and alkyd resins and also two-component polyurethane resins.

The homopolymeric or copolymeric stabilisers are added to the plastics in a concentration of 0.05 to 5% by weight, based on the material to be stabilised. Preferably, 0.1 to 2.5% by weight of the compounds, based on the material to be stabilised, are incorporated into the latter.

Incorporation can be effected after polymerisation, for example by mixing the compounds and, if desired, further additives into the melt by the methods customary in the art, before or during shaping or also by applying the dissolved or dispersed compounds to the polymer, with subsequent evaporation of the solvent if necessary.

The novel compounds can also be added to the plastics to be stabilised in the form of a master batch which contains these compounds, for example in a concentration of 2.5 to 25% by weight.

The invention therefore also relates to the plastics which are stabilised by the addition of 0.01 to 5% by weight of a compound of the formula (I) and which, if desired, can also contain other known and customary additives. The plastics stabilised in this way can be used in very diverse forms, for example as sheets, fibres, tapes or profiles or as binders for lacquers, adhesives or putties.

Further additives, together with which the stabilisers which can be used according to the invention can be employed, are, for example: antioxidants, such as 2,6-dialkylphenols derivatives of alkylated hydroquinones, hydroxylated thiodiphenyl ethers, alkylidene-bisphenols, O—, N— and S-benzyl compounds, hydroxybenzylated malonates, hydroxybenzyl-aromatic compounds, 2-triazine compounds, amides of β-(3,5-di-tert.-butyl-4-hydroxyphenyl)-propionic acid, esters of β-(3,5-di-tert.-butyl-4-hydroxphenyl)-propionic acid, esters of β-(5-tert.-butyl-4-hydroxy-3-methylphenyl)-propionic acid, esters of 3,5-di-tert.-butyl-4-hydroxyphenylacetic acid, acylaminophenols, benzylphosphonates and aminoaryl derivatives, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids, and acrylates, and also nickel compounds, sterically hindered amines, oxalic acid diamides, metal deactivators, phosphites, compounds which destroy peroxide, polyamide stabilisers, basic co-stabilisers, PVC stabilisers, nucleating agents or other additives, for example plasticisers, lubricants, emulsifiers, fillers, carbon black, asbestos, kaolin, talc, glass fibres, pigments, fluorescent brighteners, flame-proofing agents and antistatic agents.

Examples of further additives, together with which the stabilisers which can be used according to the invention can be employed, are given on pages 18 to 24 of German Offenlegungsschrift No. 2,427,853.

The following examples serve to illustrate the present invention:

EXAMPLE 1

16.3 g (0.04 mol) of 2-[(2'-hydroxy-3'-acrylamidomethyl-5'-tert.-octyl)-phenyl]-benztriazole (melting point 162° to 163° C.) and 13.5 g (0.06 mol) of distilled 4-acryloyloxy-1,2,2,6,6-pentamethyl-piperidine (boiling point: 52° to 54°/0.02 mm Hg) in 120 ml of pure benzene were initially introduced into a reaction vessel provided with a reflux condenser, a dropping funnel, a thermometer, a gas inlet tube and a stirrer (after flushing with argon) and the solution was warmed rapidly to 77° to 78° C. A solution of 0.15 g of α,α-azoisobutyronitrile (dissolved in 5 ml of pure benzene) was added dropwise at this temperature in the course of about 5 minutes, with stirring, and the internal temperature rose to 79° to 80° C. The polymerisation solution was then stirred for a further 16 hours at 77° to 78° C. A further 0.15 g of α,α-azosiobutyronitrile in 5 ml of benzene was then added and the resulting mixture was stirred for a further 24 hours at about 77° to 78° C.

In order to isolate the copolymer, the reaction solution was poured slowly, and with vigorous stirring with a turbine stirrer, into 600 ml of methanol at −30° C. and the mixture was kept at this temperature by cooling. After stirring with the turbine stirrer for about 30 minutes, the copolymer, which had precipitated as a fine pwoder, was filtered off rapidly, washed with methanol at −30° C., filtered off with suction and dried in a vacuum cabinet, first at room temperature and then at 80° to 90° C. The copolymer thus obtained has a softening point of about 145° C. and an average molecular weight ($M_n$) of 31,600. $\lambda_{max}$ 304 and 340 nm. (Additive 1)

EXAMPLES 2 TO 5

The following copolymers were prepared analogously to the method described in Example 1:

(Frequently reaction times considerably shorter than those indicated in Example 1 sufficed in these examples):

| Example | Monomer | Molar ratio A:B | Solvent | Copolymer: Sp=softening point $M_n$=molecular weight |
|---|---|---|---|---|
| 2 | (A) 1,2,2,6,6-pentamethyl-4-acryloyloxy-piperidine (B) 2-(2'-hydroxy-3'-acryloylamidomethyl-5'-sec.-butylphenyl)-benztriazole | 3:2 | benzene | Sp: ~ 145° C. $M_n$: 52,000 |
| 3 | (A) 1,2,2,6,6-pentamethyl-4-acryloyloxy-piperidine (B) 2-(2'-hydroxy-3'-methacryloyl-amidomethyl-5'-methylphenyl)-benztriazole | 2:1 | benzene | Sp: ~ 120° C. $M_n$: ~ 7,100 |
| 4 | (A) 1,2,2,6,6-pentamethyl-4-acryloyloxy-piperidine (B) 2-(2'-hydroxy-3'-acryloylamidomethyl-5'-methylphenyl)-benztriazole | 2:1 | dioxan | Sp: ~ 150° C. $M_n$: ~ 10,000 |
| 5 | (A) 1-benzyl-2,2,6,6-tetramethyl-4-acryloyloxy-piperidine (B) 2-hydroxy-4-(2'-acryloyloxyethoxy)-benzophenone | 1:1 | benzene | Sp: ~ 108° C. (melting point: ~ 130 to 132° C.) $M_n$: 11,400 |
| 6 | (A) 1-acryloyloxyethyl-2,2,6,6-tetramethylpiperidine (B) 2-(2'-hydroxy-3'-acryloylamidomethyl-5'-methylphenyl)-benztriazole | 3:2 | dioxan | Sp: ~ 125° C. $M_n$: 3,300 |

-continued

| Example | Monomer | Molar ratio A:B | Solvent | Copolymer: Sp: softening point $\overline{M}_n$: molecular weight |
|---|---|---|---|---|
| 7 | (A) 1,2,2,6,6-pentamethyl-4-acryloyloxy-piperidine  (B) 2-(2'-hydroxy-3'-acryloylamidomethyl-5'-t.butylphenyl)-benztriazole | 1:1 | benzene/ dioxan | Sp: ~ 175° C. $\overline{M}_n$: 13,500 |
| 8 | (A) 1-acryloyloxyethyl-2,2,6,6-tetramethyl-piperidine  (B) 2-(2'-hydroxy-3'-acryloylamidomethyl-5'-t-butylphenyl)-benztriazole | 1:1 | benzene/ dioxan | Sp.: ~ 150° C. $\overline{M}_n$: 7,600 |
| 9 | (A) 1-acryloyloxyethyl-2,2,6,6-tetramethyl-piperidine  (B) 2-(2'-hydroxy-3'-acryloylamidomethyl-5'-methylphenyl)-benztriazole  (C) ethyl acrylate | 1:1:1 | dioxan | Sp: ~ 100° C. $\overline{M}_n$: 6,400 |
| 10 | (A) 1,2,2,6,6-pentamethyl-4-acryloyloxy-piperidine  (B) 2-hydroxy-4-acryloyl-oxyethoxy-benzophenone | 6:5 | benzene | Sp: ~ 108° C., $\overline{M}_n$: 11,400 |
| 11 | (A) 1-acryloyloxyethyl-2,2,6,6-tetramethyl-piperidine  (B) 2-hydroxy-4-acryloyl-oxy-benzophenone | 4:5 | benzene | Sp: ~ 135° C. $\overline{M}_n$: 6,300 |
| 12 | (A) 1-acryloyloxyethyl-2,2,6,6-tetramethyl-piperidine  (B) 2-hydroxy-4-acryloyl-oxyethoxy-benzophenone | 1:1 | benzene | Sp: ~ 86° C. $\overline{M}_n$: 6,100 |
| 13 | (A) 1-n-butyl-2,2,6,6-tetramethyl-4-acryloyl-oxy-piperidine  (B) 2-hydroxy-4-acryloyloxyethoxy-benzophenone | 1:1 | benzene | Sp: ~ 110° C. $\overline{M}_n$: 12,500 |
| 14 | (A) 1,2,2,6,6-pentamethyl-4-acryloyloxy-piperidine  (B) 2-hydroxy-4-acryloyloxyethoxy-benzophenone | 1:1 | benzene | Sp: ~ 105° C. $\overline{M}_n$: 34,600 |
| 15 | (A) 1,2,2,6,6-pentamethyl-4-acryloyloxy-piperidine  (B) 2-hydroxy-4-acryloyloxyethoxy-benzophenone | 1:1 | benzene | Sp: ~ 82° C. $\overline{M}_n$: 4,400 |
| 16 | (A) 1-acryloyloxyethyl-2,2,6,6-tetramethyl-piperidine  (B) 2-hydroxy-4-acryloyloxy-2'-hydroxypropoxy-benzophenone | 1:1 | benzene | Sp: ~ 74° C. $\overline{M}_n$: 3,700 |
| 17 | (A) 1,2,2,6,6-pentamethyl-4-acryloyloxy-piperidine  (B) 2-hydroxy-4-acryloyloxybenzophenone | 3:2 | benzene | Sp: ~ 140° C. $\overline{M}_n$: 16,000 |
| 18 | (A) 1,3,8-triaza-2,4-dioxo-3-n-butyl-7,7,9,9-tetramethyl-8-acryloyloxyethyl-spiro-[4,5]-decane  (B) 2-hydroxy-4-acryloyloxybenzophenone | 1:1 | benzene | Sp: ~ 132° C. $\overline{M}_n$: 15,200 |
| 19 | (A) 1-acryloyloxyethyl-2,2,6,6-tetramethyl-piperidine | 1:1 | benzene | Sp: ~ 95° C. |
|  | (B)ethyl 4-acryloyloxy-benzylidene cyanoacetate |  |  | $\overline{M}_n$: 5,800 |
| 20 | (A) 1-benzyl-2,2,6,6-tetramethyl-4-acryloyloxy-piperidine  (B) ethyl 4-acryloyloxy-benzylidene cyanoacetate | 1:1 | benzene | Sp: ~ 125° C. $\overline{M}_n$: 4,200 |
| 21 | (A) 1-acryloyloxy-2,2,6,6-tetramethyl-piperidine  (B) dimethyl 4-acryloyloxy-benzylidene malonate | 1:1 | benzene | Sp: ~ 90° C. $\overline{M}_n$: 23,800 |
| 22 | (A) 1,2,2,6,6-pentamethyl-4-methacryloyloxy-piperidine  (B) dimethyl 4-acryloyloxy-benzylidene malonate | 1:1 | benzene | Sp: ~ 120° C. $\overline{M}_n$: 10,700 |
| 23 | (A) 1,2,2,6,6-pentamethyl-4-acryloyloxy-piperidine  (B) 1',2',2',6',6'-pentamethylpiperidin-4'-yl 4-acryloyloxy-benzylidene-cyanoacetate | 1:1 | benzene | Sp: ~ 150° C. $\overline{M}_n$: 5,800 |
| 24 | (A) 1-acryloyloxyethyl-2,2,6,6-tetramethyl-piperidine  (B) ethyl 2-cyano-3-methyl-3-(4'-acryloyl-oxyphenyl)-acrylate | 1:1 | benzene | Sp: ~ 105° C. $\overline{M}_n$: 6,900 |
| 25 | (A) 1-acryloyloxyethyl-2,2,6,6-tetramethyl-piperidine  (B) dimethyl 4-acryloyloxyethoxy-benzylidene-cyanoacetate | 2:1 | benzene | Sp: ~ 76° C. $\overline{M}_n$: 11,500 |
| 26 | (A) 1-acryloyloxyethyl-2,2,6,6-tetramethyl-piperidine  (B) di-(1',2',2',6',6'-pentamethylpiperidin-4'-yl) 4-acryloyloxy-benzylidene-malonate | 3:2 | benzene | Sp: 102° C. $\overline{M}_n$: 7,000 |

What is claimed is:

1. A copolymeric compound useful as a light stabilizer and UV absorber in organic materials which carries side N-heterocyclic rings and contains the recurring structural unit of the formula (I)

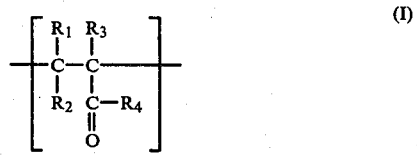

(I)

in which $R_1$ and $R_2$ are hydrogen and $R_3$ is hydrogen or $C_1$–$C_4$ alkyl and $R_4$ is a N-heterocyclic substituent of the formulae (II), (III), (IV) or (V)

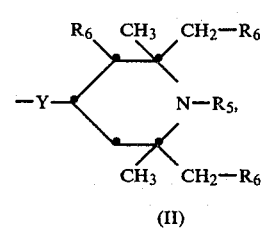

(II)

-continued

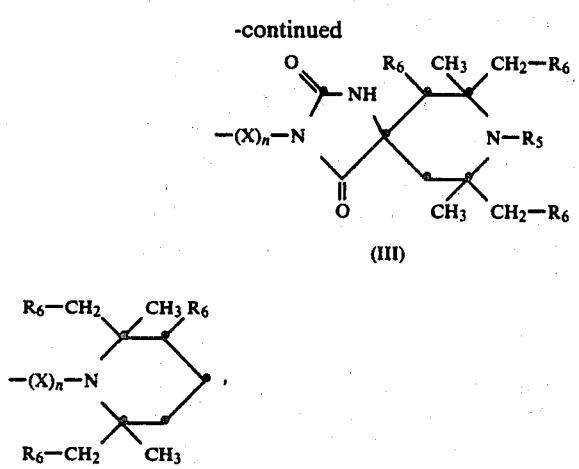

(III)

(IV)

(V)

in which $R_5$ is hydrogen, oxyl, $C_1$-$C_{18}$ alkyl, $C_3$-$C_8$ alkenyl, $C_3$-$C_6$ alkynyl, $C_7$-$C_{12}$ aralkyl, $C_2$-$C_{21}$ alkoxyalkyl, cyanomethyl, an aliphatic acyl group having 1 to 4 carbon atoms or a group —$CH_2COOR_7$, in which $R_7$ is $C_1$-$C_{12}$ alkyl, $C_3$-$C_8$ alkenyl, phenyl, $C_7$-$C_8$ aralkyl or cyclohexyl, and $R_6$ is hydrogen or methyl and Y is —O— or $$-\overset{|}{N}-R_9,$$

in which $R_9$ is hydrogen, $C_1$-$C_{12}$ alkyl, $C_5$-$C_8$ cycloalkyl or $C_7$-$C_{12}$ aralkyl, and X is a group of the formula —O—CH($R_{10}$)—$CH_2$— (VI), in which $R_{10}$ is hydrogen, methyl, ethyl, phenoxymethyl or phenyl, and n is 0 or 1, and $R_{11}$ is $C_1$-$C_{18}$ allyl, cyclohexyl, phenyl, benzyl or a group of the formula —$CH_2$—$COOR_{12}$ (VII), in which $R_{12}$ is $C_1$-$C_8$ alkyl, and, furthermore, $R_4$ is one of the groups of the formulae (VIII), (IX), (X) or (XI)

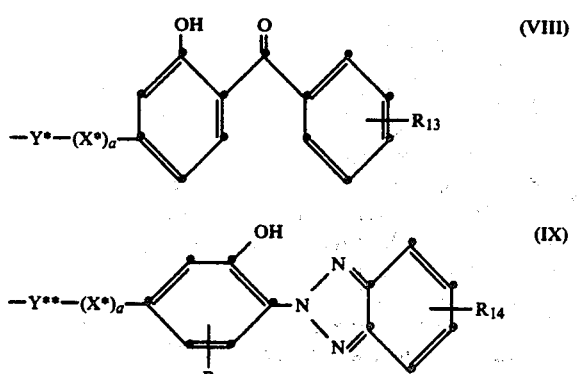

-continued

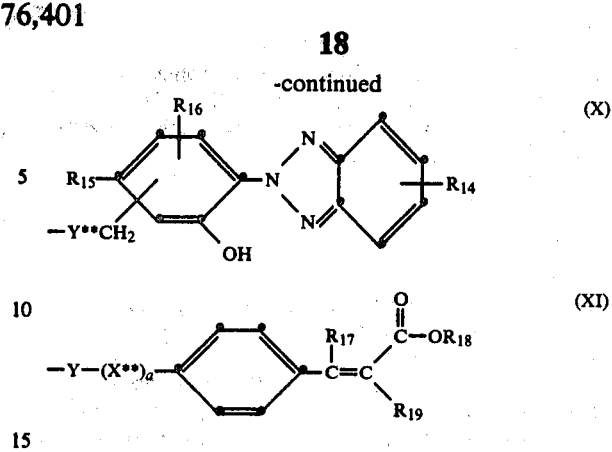

in which Y and Y☆☆ have the meaning defined above for Y, and Y☆ is —O— or $$-\overset{|}{N}-R_{9\text{☆}},$$

in which $R_{9☆}$ is hydrogen or $C_1$-$C_8$ alkyl, and X☆ is a group of the formula —CH($R_{10}$)—$(CH_2)_b$—O— (XII), in which b is 1 or 2 and $R_{10}$ is as defined above, and a is 0 or 1, and $R_{13}$ is hydrogen, methyl or chlorine and $R_{14}$ is hydrogen, methyl, methoxy or chlorine and $R_{15}$ is hydrogen or hydroxyl and $R_{16}$ is H, $C_1$-$C_{12}$ alkyl, $C_5$-$C_8$ cycloalkyl, phenyl, $C_7$-$C_{12}$ aralkyl or chlorine and X ☆☆ is a group of the formula (XII), in which $R_{10}$ is as defined above and b is 1, and $R_{17}$ is hydrogen or $C_1$-$C_4$ alkyl and $R_{18}$ is $C_1$-$C_{12}$ alkyl, $C_5$-$C_8$ cycloalkyl or a group of the formula (XIII)

(XIII)

in which $R_5$☆ is hydrogen, $C_1$-$C_8$ alkyl, $C_3$-$C_8$ alkenyl, $C_7$-$C_{12}$ aralkyl or an aliphatic acyl group having 1 to 4 carbon atoms and $R_6$ is as defined above, and $R_{19}$ is —CN or a group of the formula —$COOR_{18}$ (XV), in which $R_{18}$ is as defined above, with the proviso that, in the copolymeric molecule containing the recurring structural unit I, at least one (A) of the substituents $R_4$ is one of the groups of the formula (II), (III), (IV) or (V) and at least one (B) of the substituents $R_4$ is one of the groups of the formulae (VIII), (IX), (X) or (XI), (A):(B) being in a ratio of 50:1 to 1:50.

2. A copolymeric compound according to claim 1, which contains the recurring structural unit of the formula (I), in which $R_1$ and $R_2$ are hydrogen and $R_3$ is hydrogen or methyl and $R_4$ is a group of the formulae (II), (III), (IV) or (V), in which $R_5$ is hydrogen, $C_1$-$C_{12}$ alkyl, allyl, propargyl, benzyl, acetyl or $C_2$-$C_6$ alkoxyalkyl and $R_6$ is hydrogen or methyl and Y is —O— or $$-\overset{|}{N}-R_9,$$

in which $R_9$ is hydrogen $C_1$-$C_{12}$ alkyl, cyclohexyl or benzyl, and X is a group of the formula (VI), in which $R_{10}$ is hydrogen, methyl or ethyl, and n is 0 or 1, and $R_{11}$ is $C_1$–$C_{12}$ alkyl, allyl or benzyl, and, furthermore, $R_4$ is a group of the formulae (VIII), (IX), (X) or (XI), in which Y and Y✩✩ have the meaning defined above for Y, and Y✩ is —O— or

in which $R_9$✩ is hydrogen or $C_1$–$C_4$ alkyl, and X✩ is a group of the formula (XII), in which $R_{10}$ is as defined above, and b is 1 or 2, and a is 0 or 1, $R_{13}$ is hydrogen, methyl or chlorine and $R_{14}$ and $R_{15}$ are hydrogen and $R_{16}$ is H, $C_1$–$C_8$ alkyl, cyclohexyl, phenyl, $C_7$–$C_9$ aralkyl or chlorine, and X✩✩ and $R_{17}$ are as defined above and $R_{18}$ is $C_1$–$C_8$ alkyl, cyclohexyl or a group of the formula (XIII), in which $R_5$✩ is hydrogen, $C_1$–$C_8$ alkyl, allyl, benzyl or acetyl and $R_6$ is as defined, and $R_{19}$ is —CN or a group of the formula (XIV), in which $R_{18}$ is as defined above.

3. A copolymeric compound according to claim 1, which contains the recurring structural unit of the formula (I), in which $R_1$ and $R_2$ are hydrogen and $R_3$ is hydrogen or methyl and $R_4$ is a group of the formula (II) or (IV), in which $R_5$ is hydrogen, $C_1$–$C_8$ alkyl, allyl, benzyl or acetyl and $R_6$ is hydrogen and Y is —O— or

in which $R_9$ is hydrogen or $C_1$–$C_4$ alkyl, and X is a group of the formula (VI), in which $R_{10}$ is hydrogen or methyl, and n is 0 or 1, and, furthermore, $R_4$ is a group of the formulae (VIII), (IX), (X) or (XI), in which Y is as defined above and Y✩✩ is

in which $R_9$ is as defined above, and Y✩ is —O— and X✩ and X✩✩ are a group of the formula (XII), in which $R_{10}$ is as defined above and b is 1, and a is 0 or 1, and $R_{13}$, $R_{14}$ and $R_{15}$ are hydrogen and $R_{16}$ is H, $C_1$–$C_8$ alkyl or $C_7$–$C_9$ aralkyl and $R_{17}$ is $C_1$–$C_4$ alkyl if $R_{19}$ is —CN or is hydrogen if $R_{19}$ is a group of the formula (XIV), and $R_{18}$ is $C_1$–$C_8$ alkyl or a group of the formula (XIII), in which $R_5$✩ is hydrogen, $C_1$–$C_4$ alkyl, benzyl or acetyl, and $R_6$ is as defined above, and $R_{19}$ is —CN or a group of the formula (XIV), in which $R_{18}$ is as defined above.

4. A copolymeric compound according to claim 1, which contains the recurring structural unit of the formula (I), in which $R_1$ and $R_2$ are hydrogen and $R_3$ is hydrogen or methyl and $R_4$ is a group of the formulae (II) or (IV), in which $R_5$ is hydrogen, $C_1$–$C_4$ alkyl, benzyl or acetyl and $R_6$ is hydrogen and Y is —O— or —$NR_9$, in which $R_9$ is hydrogen or $C_1$–$C_4$ alkyl, and X is a group of the formula (VI), in which $R_{10}$ is hydrogen or methyl, and n is 0 or 1, and, furthermore, $R_4$ is a group of the formulae (VIII), (X) or (XI), in which Y and Y are —O— and Y✩✩ is

in which $R_9$ is as defined above, and X✩ and X✩✩ are a group of the formula (XII), in which $R_{10}$ is as defined above and b is 1, and a is 0 or 1, and $R_{13}$, $R_{14}$ and $R_{15}$ are hydrogen and $R_{16}$ is H, $C_1$–$C_8$ alkyl or $C_7$–$C_9$ aralkyl and $R_{17}$ is methyl if $R_{19}$ is —CN or is hydrogen if $R_{19}$ is a group of the formula XIV), and $R_{18}$ is $C_1$–$C_8$ alkyl or a group of the formula (XIII), in which $R_5$✩ is hydrogen or methyl and $R_6$ is hydrogen, and $R_{19}$ is —CN or a group of the formula (XIV), in which $R_{18}$ is as defined above.

5. A copolymeric compound according to claim 1, which contains the recurring structural unit of the formula (I), in which $R_1$ and $R_2$ are hydrogen and $R_3$ is hydrogen or methyl and $R_4$ is a group of the formulae (II) or (IV), in which $R_5$ is hydrogen, methyl or acetyl and $R_6$ is hydrogen and Y is —O— or

in which $R_9$ is hydrogen or $C_1$–$C_4$ alkyl, and X is a group of the formula (VI), in which $R_{10}$ is hydrogen, and n is 0 or 1, and, furthermore, $R_4$ s a group of the formulae (VIII) or (X), in which Y✩ is —O— and Y is as defined above and X✩ and X ✩✩ are a group of the forula (XII), in which $R_{10}$ is as defined above and b is 1 and a is 0 or 1, and $R_{13}$, $R_{14}$ and $R_{15}$ are hydrogen and $R_{16}$ is H, $C_1$–$C_8$ alkyl or $C_7$–$C_9$ aralkyl.

6. A copolymeric compound according to claim 1, of the formula I, in which $R_1$, $R_2$ and $R_3$ are hydrogen and $R_4$ is a group of the formula IV, in which $R_6$ is hydrogen, and X is a group of the formula VI, in which $R_{10}$ is hydrogen and n is 1, or $R_4$ is also a group of the formula X, in which $R_{14}$ and $R_{15}$ are hydrogen and $R_{16}$ is t.-butyl in the p-position relative to the hydroxyl group, and Y✩✩ is —O—.

7. A copolymeric compound according to claim 1, of the formula I, in which $R_1$, $R_2$ and $R_3$ are hydrogen and $R_4$ is a group of the formula IV, in which $R_6$ is hydrogen, and X is a group of the formula VI, in which $R_{10}$ is hydrogen and n is 1, or $R_4$ is also a group of the formula VIII, in which $R_{13}$ is hydrogen, and X✩ is a group of the formula XII, in which b is 1 and $R_{10}$ is hydrogen, and, furthermore, Y✩ is —O—.

8. A copolymeric compound according to claim 1, of the formula I, in which $R_1$, $R_2$ and $R_3$ are hydrogen and $R_4$ is a group of the formula IV, in which $R_6$ is hydrogen, and X is a group of the formula VI, in which $R_{10}$ is hydrogen and n is 1, or $R_4$ is also a group of the formula VIII, in which $R_{13}$ is hydrogen and a is 0 and Y✩ is —O—.

9. A copolymer compound according to claim 1, of the formula I, in which $R_1$, $R_2$ and $R_3$ are hydrogen and $R_4$ is a group of the formula IV, in which $R_6$ is hydrogen, and X is a group of the formula VI, in which $R_{10}$ is hydrogen and n is 1, or $R_4$ is also a group of the formula XI, in which $R_{17}$ is hydrogen, and $R_{18}$ is a group of the formula XIII, in which $R_5$✩ is methyl and $R_6$ is hydrogn, and $R_{19}$ is a group of the formula XIV, in which $R_{18}$ is as defined above and a is 0 and Y is —O—.

10. A process for the preparation of a compound according to claim 1, which comprises the free radical, ionic or photo-initiated polymerisation of a monomer of the formula (XVa)

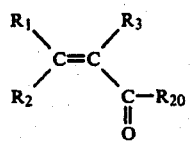
(XVa)
with a monomer of the formula (XVb)
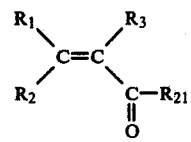
(XVb)
in which formulae $R_{20}$ is a group of the formulae (II), (III), (IV) or (V), $R_{21}$ is a group of the formulae (VIII), (IX), (X) or (XI) and these groups and also the substituents $R_1$, $R_2$ and $R_3$ are as defined in claim 1.
11. The process of claim 10 which is conducted in the presence of additional copolymerizable monomers.
* * * * *